United States Patent [19]

Petrick et al.

[11] Patent Number: 5,352,884
[45] Date of Patent: Oct. 4, 1994

[54] METHOD AND APPARATUS FOR PROVIDING OFFSET FOR LIGHT DETECTOR

[75] Inventors: Scott W. Petrick, Pewaukee; Paul R. Granfors, Milwaukee, both of Wis.

[73] Assignee: General Electric Corporation, Schenectady, N.Y.

[21] Appl. No.: 48,118

[22] Filed: Apr. 14, 1993

[51] Int. Cl.⁵ .............................................. H01J 40/14
[52] U.S. Cl. .................................. 250/208.1; 348/308
[58] Field of Search ............ 250/208.1, 214 R, 370.08, 250/370.09; 348/308

[56] References Cited

U.S. PATENT DOCUMENTS

| | | | |
|---|---|---|---|
| 4,959,723 | 9/1990 | Hashimoto | 348/308 |
| 4,996,413 | 2/1991 | McDaniel et al. | 250/208.1 |
| 5,184,018 | 2/1993 | Conrads et al. | 250/208.1 |

*Primary Examiner*—David C. Nelms
*Attorney, Agent, or Firm*—Michael, Best & Friedrich

[57] ABSTRACT

The invention provides a solid state light imager or x-ray detector including an array of rows and columns of elements, each element including a photo diode, which converts photons to an electrical signal, and a transistor. Each photo diode has a capacitance associated with it. The cathode of the photo diode in each element is connected to the source of the transistor in the element. The amount of charge removed from each photo diode, after exposure to light, is used to create an image. The imager is capable of accurate measurement of charge removed from the photo diodes after the array has been exposed to light, using unipolar measuring circuitry, in spite of charge retention by the transistors and a problem caused by the combination of changes in row voltage and parasitic row to column capacitance.

20 Claims, 4 Drawing Sheets

METHOD AND APPARATUS FOR PROVIDING OFFSET FOR LIGHT DETECTOR

BACKGROUND OF THE INVENTION

The invention relates to methods of and apparatus for detecting light. More particularly, the invention relates to light imaging using an array of photo detectors.

It is known to manufacture solid state light imagers or x-ray detectors using an array of rows and columns of photo detector elements. See for example U.S. Pat. No. 4,996,413, issued to McDaniel et al. on Feb. 26, 1991, which is incorporated herein by reference. Each element includes a photo diode, which converts photons to an electrical signal, and a transistor. Each photo diode has a capacitance associated therewith. The cathode of the photo diode in each element is connected to the source of the transistor in the element. The anodes of all the photo diodes are connected together and to a negative bias voltage $-V_b$. The drains of transistors in respective columns are connected to respective column electrodes, and the gates of transistors in respective rows are connected to respective row electrodes.

To acquire an image from the array, the column electrodes are connected to a known, stable voltage $V_c$. While the column electrodes are connected to the voltage $V_c$, the row electrodes are connected to a voltage $V_{on}$ which is positive relative to $V_c$. The photo diodes will be back biased. The transistors will conduct and a charge will be placed on each of the capacitances associated with the photo diodes. After the diodes have been charged, the row electrodes are connected to a voltage $-V_{off}$ which is negative relative to both $V_c$ and $-V_b$ to turn the transistors off and prevent them from conducting. The array is then exposed to light energy, such as produced by a scintillator which is exposed to x-rays. The photo diodes will conduct and the capacitance associated with each photo diode will be partially discharged. The amount of charge removed from the capacitance associated with each photo diode will depend on the intensity and duration of the light energy striking that particular photo diode. If the duration of light energy is the same for each of the photo diodes, as is the case when an x-ray exposure is made, then the amount of charge removed from the capacitance associated with the photo diodes will represent the intensity of the light energy striking the various photo diodes, and can be read by measuring the amount of charge required to restore each photo diode's capacitance. The charges measured for restoring the capacitances can therefore be used to create an image.

SUMMARY OF THE INVENTION

The invention provides a solid state light imager or x-ray detector including an array of rows and columns of elements, the elements including photo diodes and transistors arranged and operated in the manner described above, which imager is capable of accurate measurement of charge removed from the photo diodes after the array has been exposed to light, using unipolar measuring circuitry, in spite of charge retention by the transistors and parasitic row to column capacitance.

Each photo diode has a capacitance associated therewith. The cathode of the photo diode in each element is connected to the source of the transistor in the element. The anodes of all the photo diodes are connected together and to a negative bias voltage $-V_b$. The drains of transistors in respective columns are connected to respective column electrodes, and the gates of transistors in respective rows are connected to respective row electrodes.

To acquire an image from the array, the column electrodes are connected to a known, stable voltage $V_c$. While the column electrodes are connected to the voltage $V_c$, the row electrodes are connected to a voltage $V_{on}$ which is positive relative to $V_c$. The photo diodes will be back biased. The transistors will conduct and a charge will be placed on each of the capacitances associated with the photo diodes. After the diodes have been charged, the row electrodes are connected to a voltage $-V_{off}$ which is negative relative to both $V_c$ and $-V_b$ to turn the transistors off and prevent them from conducting. The array is then exposed to light energy, such as produced by a scintillator which is exposed to x-rays. The photo diodes will conduct and the capacitance associated with each photo diode will be partially discharged. The amount of charge removed from the capacitance associated with each photo diode will depend on the intensity and duration of the light energy striking that particular photo diode. The amount of charge removed from the capacitance associated with each photo diode is measured by connecting the rows, one at a time, to the voltage $V_{on}$ and respectively measuring the charge required, at the column electrode for each diode in the row, to restore the diodes' capacitance to its voltage before exposure to the light energy. In this regard, a sensing circuit, including an integrator for example, is provided for each column. Each row is returned to $-V_{off}$ after being read, and the sensing circuits are all cleared (e.g., integrators are reset) after a row has been read so as to prepare the sensing circuits for reading the next row.

The inventors of the present invention have recognized that because the output signal from the array is very small, circuitry for measuring charge removed from the photo diodes is very sensitive. The transistors exhibit "charge retention," and not all signal leaves the transistors when a row is returned to $-V_{off}$. The charge retained by the transistors in a row being read has the effect of a negative offset for the elements being read in the row. If the sensing circuit is unipolar (i.e., operates in one direction only from zero), the negative offset could cause the sensing circuit to generate false readings or to saturate. Even if the sensing circuit is bipolar, if autoranging is employed in the conversion process (where the conversion is always to a given number of levels, but the conversion range and resolution are both dependent upon the amplitude of a signal being converted), the negative offset may be large enough to leave the sensing circuit in a less sensitive range. This would cause a reduction in gray scale resolution and could cause "cartooning" in the darker areas of the resulting image. Cartooning is known in the art as large areas with discrete grey levels, instead of a smooth transition in gray levels, in the resulting image.

The inventors of the present invention have also recognized that there is parasitic capacitance from a column to a row. When row voltage is changed from $-V_{off}$ to $V_{on}$, this parasitic capacitance causes charge to appear at the column electrodes in the form of large offsets opposite in direction from signal. The offsets caused by the parasitic column to row capacitance can also cause false readings by the measuring circuit due to saturation of the measuring circuit.

The inventors of the present invention have not only identified the above stated problems, but have also provided solutions to these problems.

More particularly, the inventors have determined that the parasitic capacitance from row to column can be used to solve both of the above stated problems. The problem caused by the change in row voltage and by the parasitic capacitance can be compensated for by providing a negative transition of equal magnitude on another row. However, it would be undesirable to turn a row off when turning a row on; e.g., it would be undesirable to provide compensation by turning a row from $V_{on}$ to $-V_{off}$ while reading another row. This is because slight differences in parasitic capacitance, switch resistance, row electrode and contact impedance, or perhaps contact imperfections from row to row, would result in some rows being inadequately compensated. Assuming a unipolar measuring circuit, if both row transitions (off to on and on to off) occur in the same acquisition period, compensation would not need to be exact but only adequate. Slight over-compensation could be tolerated, as long as the compensation does not send the measuring circuit into saturation at the maximum end. Under-compensation cannot be tolerated at all because the measuring circuit, being unipolar, will saturate immediately at even slightly below its minimum of zero.

But all that is needed, to compensate for the parasitic capacitance during the positive transition on a row from $-V_{off}$ to $V_{on}$, is a negative transition on another row of equal magnitude. Therefore, in the preferred embodiment of the invention, the charge on the columns caused by the parasitic capacitance during the positive transition on a row from $-V_{off}$ to $V_{on}$ is compensated by turning another row off harder to provide a negative transition of equal magnitude; e.g., a row other than the row being read is provided with a transition from $-V_{off}$ to a voltage which is more negative than $-V_{off}$. In order to minimize the range of voltages required by the array, a number of rows could be used to provide the compensation, and the magnitude of the negative transition provided on the number of rows would be scaled down by the ratio of rows providing compensation to the magnitude of the transition at the row being turned on from $-V_{off}$ to $V_{on}$.

A similar solution is provided for the charge retention problem. More particularly, the solution to the charge retention problem is identical to the solution to the parasitic capacitance problem except that the timing and magnitude of transitions for offsetting the charge retention are different from the timing and magnitude of transitions for compensating for parasitic capacitance. The magnitude will depend on the amount of charge retained.

Certain of the rows can be used to provide compensation for parasitic capacitance, and other rows can be used to provide offset for charge retention. The rows not being read can be divided up in any manner to provide compensation and offset. It is also possible that one row could be used to provide both compensation and offset. (Or, if it is desired to minimize the range of voltages required by the array, a set of rows could be used, with the magnitude of transitions reduced at each row of the set, and this set of rows could be used to provide both compensation and offset.)

Other features and advantages of the invention will become apparent to those of ordinary skill in the art upon review of the following detailed description, claims, and drawings.

Figure 1:
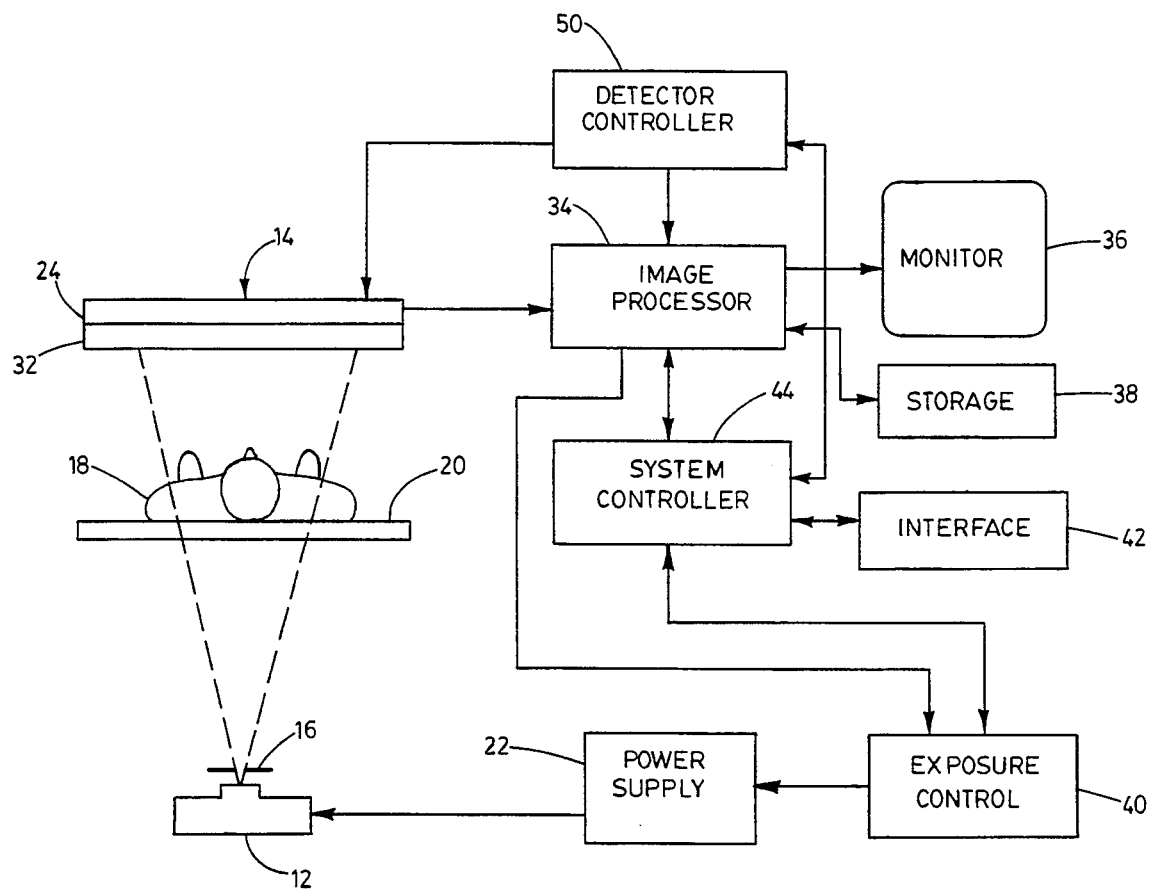
FIG. 1 is a block diagram illustrating use of a light imaging system embodying various of the features of the invention.
Figure 2:
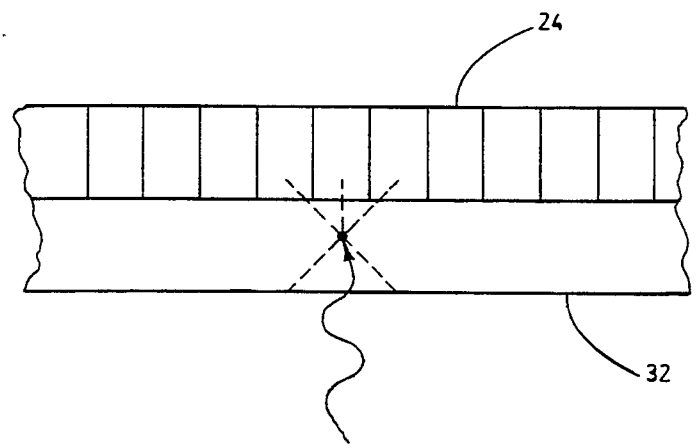
FIG. 2 is a block diagram illustrating an array of photo detectors included in the system of FIG. 1.

Before one embodiment of the invention is explained in detail, it is to be understood that the invention is not limited in its application to the details of construction and the arrangement of components set forth in the following description or illustrated in the drawings. The invention is capable of other embodiments and of being practiced or carried out in various ways. Also, it is to be understood that the phraseology and terminology used herein is for the purpose of description and should not be regarded as limiting.

DETAILED DESCRIPTION OF THE PREFERRED EMBODIMENT OF THE INVENTION

Shown in FIG. 1 is an imaging system 10 including an x-ray tube 12, an x-ray detector 14, and a collimator 16. X-rays are transmitted from the x-ray tube 12, via the collimator 16, to the x-ray detector 14. An x-ray of a patient 18 is taken by placing the patient 18 between the collimator 16 and the x-ray detector 14, placing x-ray transmissive material 20 on the side of the patient 18 facing the collimator 16, and exposing the patient 18 to x-rays for an amount of time.

The imaging system 10 further includes a power supply 22 for exciting the x-ray tube 12.

Figure 3:
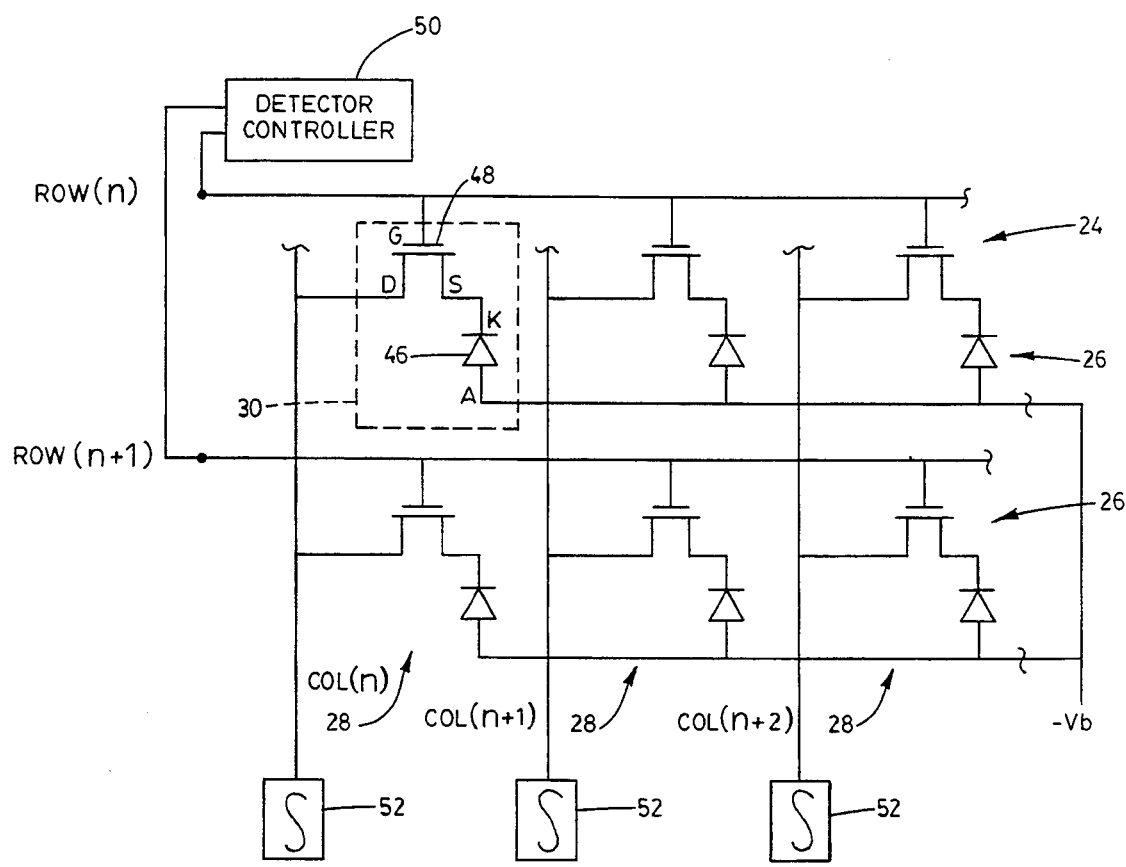
FIG. 3 is a circuit diagram, partially broken away, illustrating the circuit components in one of the arrays of FIG. 2.

As shown in FIG. 3, the x-ray detector 14 includes an array 24 of rows 26 and columns 28 of photo detector elements 30. The detector 14 further includes a scintillator 32 between the array 24 and the patient 18, and, more particularly, abutting the array 24, which scintillator converts x-rays to light.

The system 10 further includes an image processor 34 that receives the output from the array 24 and which processes the image received by the array 24. The system 10 further includes a monitor 36 connected to the image processor 34, for displaying the processed image, and includes an image storage device 38 for archiving the processed image if desired. The system 10 further includes an exposure control circuit 40 which receives a brightness signal from the image processor 34 and which regulates the power supply 22 to regulate x-ray exposure.

The system 10 further includes an operator interface 42, and a system controller 44 which controls the operation of the rest of the system 10, and which receives commands from a human operator via the operator interface 42.

The array 24 is made of layers of thin film material including one or more layers of amorphous silicon. As shown in FIG. 3, each photo detector element 30 of the array 24 includes a photo diode 46 which converts photons to an electrical signal. Each photo diode 46 has an anode A and a cathode K, and is a large area photo diode taking up most of the area in each element 30 so as to intercept a large fraction of the light that hits the element 30. Each element 30 further includes a thin film transistor 48. In the illustrated embodiment, each transistor 48 is a Field Effect Transistor (FET) having a gate G, a drain D, and a source S. Each photo diode has a capacitance associated therewith.

The cathode K of the photo diode 46 in each element 30 is connected to the source of the transistor in the element. The anodes A of all the photo diodes 46 in the array 24 are connected together and to a negative bias voltage $-V_b$. The drains D of transistors in respective columns are connected to respective column electrodes COL(n), COL(n+1), COL(n+2) . . . , and the gates of transistors in respective rows are connected to respective row electrodes ROW(n), ROW(n+1) . . .

The system 10 further includes a detector controller 50 connected to the system controller 44 and to the row electrodes and column electrodes. The column electrodes are also connected to the image processor 34.

To acquire an image from the array, the detector controller 50 connects the column electrodes to a known, stable voltage $V_c$, which for example is within two volts of ground. While the column electrodes are connected to the voltage $V_c$, the detector controller 50 connects the row electrodes to a voltage $V_{on}$ which is positive relative to $V_c$. The photo diodes will be back biased. The transistors will conduct and a charge will be placed on each of the capacitances associated with the photo diodes. After the diodes have been charged, the detector controller 50 connects the row electrodes to a voltage $-V_{off}$ which is negative relative to both $V_c$ and $-V_b$ to turn the transistors off and prevent them from conducting. The array is then exposed to light energy, such as produced by the scintillator 32 being exposed to x-rays. The photo diodes will conduct and the capacitance associated with each photo diode will be partially discharged. The amount of charge removed from the capacitance associated with each photo diode will depend on the intensity and duration of the light energy striking that particular photo diode. Because the duration of exposure to light energy is the same for each of the photo diodes, the amount of charge removed from the capacitance associated with the photo diodes represents the intensity of the light energy striking the various photo diodes, and is read by measuring the amount of charge required to restore each photo diode's capacitance. The variation in charge removed from different photo diodes constitutes an image of the light striking the detector.

The amount of charge removed from the capacitance associated with each photo diode is measured by instructing the detector controller 50 to connect the rows, one at a time, to the voltage $V_{on}$ and respectively measuring the charge required, at the column electrode for each diode in the row, to restore the diodes' capacitance to its voltage before exposure to the light energy. In this regard, the image processor 34 includes a sensing circuit, including an integrator 52 in the preferred embodiment, connected to each column. The integrator 52 is preferably a low noise integrator without offset or input bias currents. The detector controller 50 returns each row to $-V_{off}$, and the sensing circuits are all cleared (e.g., integrators are reset) after a row has been read so as to prepare the sensing circuits for reading the next row.

Figure 4:
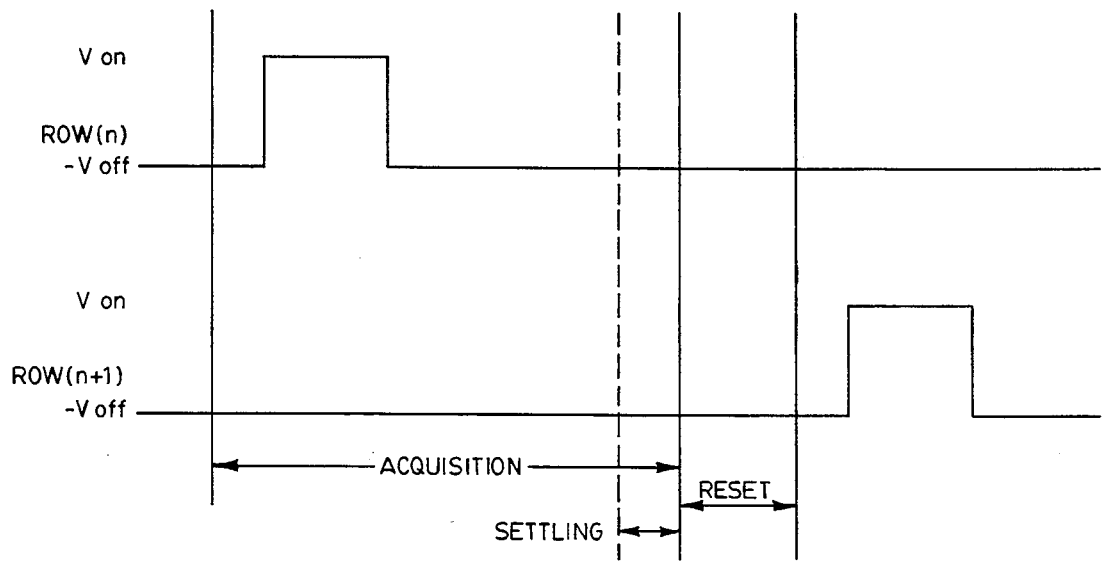
FIG. 4 is a timing diagram illustrating the use of the array of FIG. 3 to acquire an image.

The period of time between the reading of one row and the reading of the next row can be described as consisting of an acquisition period, and a reset period (during which the integrator is reset). The acquisition period and the reset period are not necessarily of the same length. Both row transitions occur during the acquisition period. As the sensing circuits have a need for settling time, the acquisition period must be longer than the length of time the row is at $V_{on}$. See FIG. 4.

Because the output signal from the array is very small, circuitry for measuring charge removed from the photo diodes is very sensitive. The transistors 48 in the array exhibit "charge retention," and not all signal leaves the amorphous silicon transistors of the array when a row is returned to $-V_{off}$. The charge retained by the transistors in a row being read has the effect of an offset, in a direction opposite to signal, for the elements being read in the row. If the sensing circuit is unipolar (i.e., operates in one direction only from zero), the negative offset could cause the sensing circuit to saturate. If the sensing circuit is an integrator that reads only in the positive direction, a negative signal cannot be read. Even if the sensing circuit is bipolar, if autoranging is employed in the conversion process (where the conversion is always to a given number of levels, but the conversion range and resolution are both dependent upon the amplitude of a signal being converted), the negative offset may be large enough to leave the sensing circuit in a less sensitive range. This would cause a reduction in gray scale resolution and could cause cartooning in the darker areas of the resulting image.

There is also parasitic capacitance from a column to a row. When row voltage is changed from $-V_{off}$ to $V_{on}$, this parasitic capacitance causes charge to appear at the column electrodes in the form of large offsets in the direction opposite to signal. The negative offsets caused by the parasitic column to row capacitance can also cause false readings by the measuring circuit and saturation of the measuring circuit.

Figure 5:
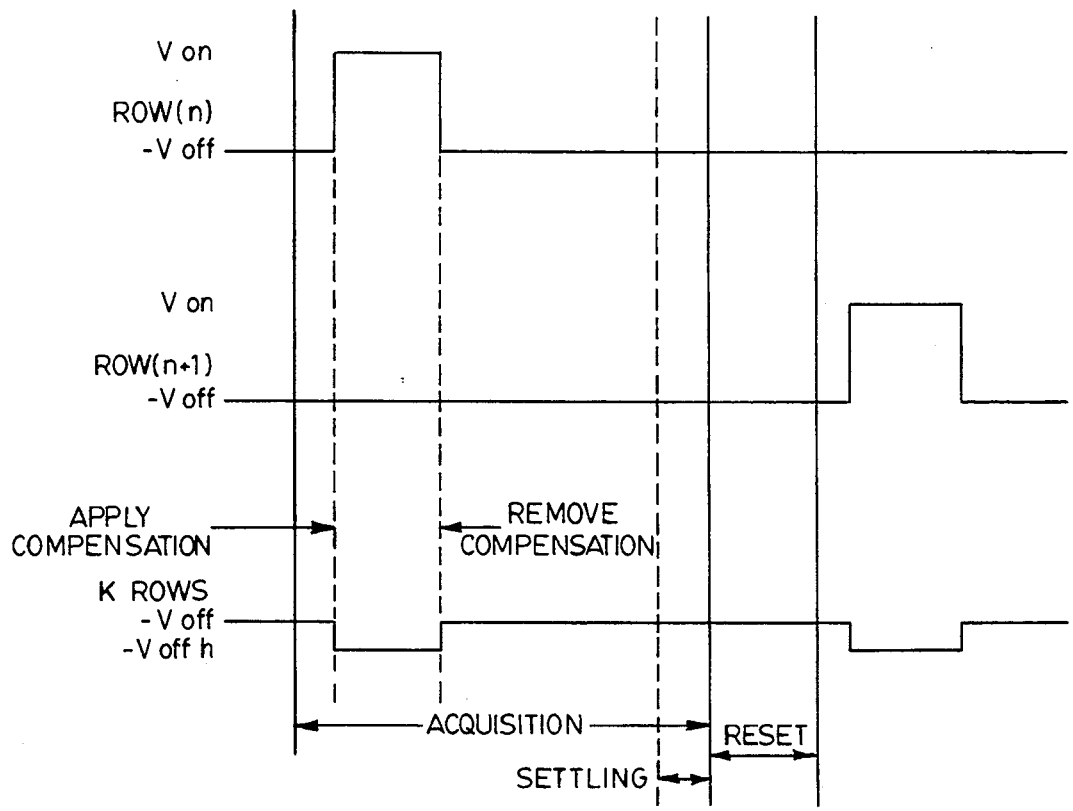
FIG. 5 is a timing diagram illustrating the application of compensation, in accordance with the invention, in the use of the array of FIG. 3.

The parasitic capacitance from row to column is used to solve both of the above stated problems. To solve the parasitic capacitance problem, the charge on the columns caused by the parasitic capacitance during the positive transition on a row from $-V_{off}$ to $V_{on}$ is compensated by providing a negative transition of equal magnitude on another row. However, it would be undesirable to turn a row off when turning a row on; e.g., it would be undesirable to provide compensation by turning a row from $V_{on}$ to $-V_{off}$ while reading another row. But all that is needed, to compensate for the parasitic capacitance during the positive transition on a row from $-V_{off}$ to $V_{on}$, is a negative transition on another row of equal magnitude. Therefore, in the preferred embodiment of the invention, the charge on the columns caused by the parasitic capacitance during the positive transition on a row from $-V_{off}$ to $V_{on}$ is compensated by instructing the detector controller 48 to turn another row off harder to provide a negative transition of equal magnitude; e.g., a row other than the row being read is provided with a transition from $-V_{off}$ to a negative voltage which is more negative than $-V_{off}$. In order to minimize the range of voltages required to be provided by the detector controller 50 to the array, a number of rows are preferably used to provide the compensation, and the magnitude of the negative transition provided on the number of rows is scaled down by the ratio of rows providing compensation to the magnitude of the transition at the row being turned on from $-V_{off}$ to $V_{on}$. For example, in the preferred embodiment illustrated in FIG. 5, a transition is made from $-V_{off}$ to a negative voltage $-V_{offh}$ simultaneously on a plurality K of rows other than the row being read, where to a first approximation the magnitude of the transition from $-V_{off}$ to $-V_{offh}$ multiplied by the number K of rows equals the magnitude of the transition at the row being read.

Figure 6:
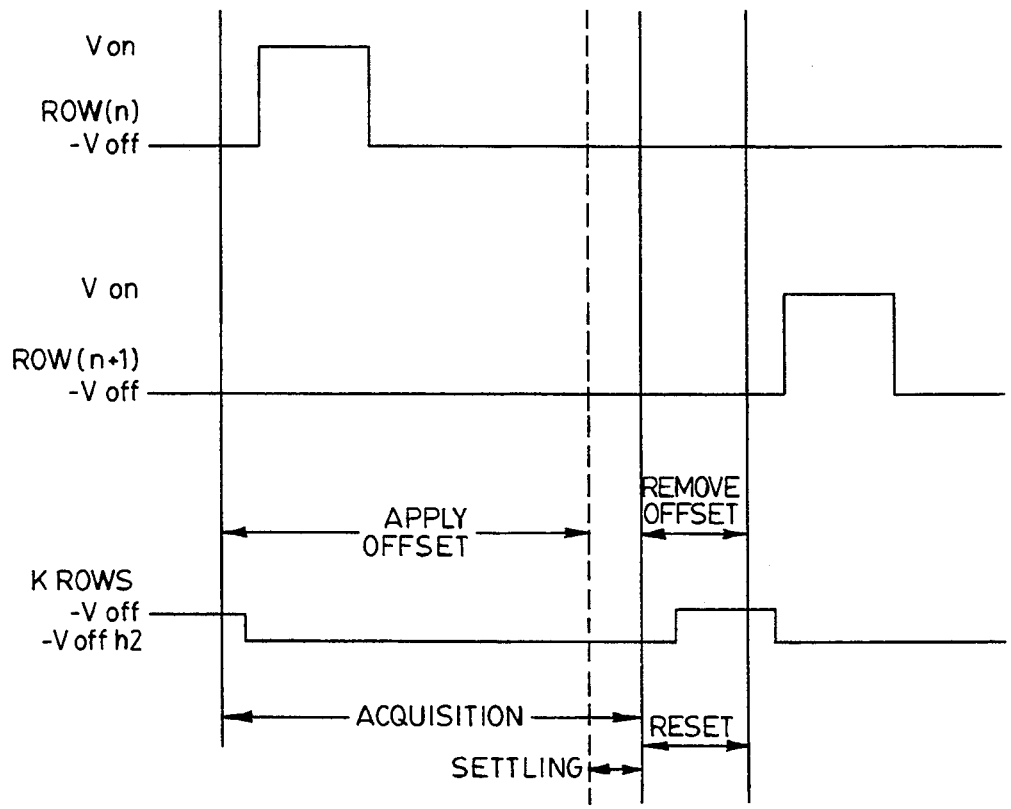
FIG. 6 is a timing diagram illustrating the application of offset, in accordance with the invention, in the use of the array of FIG. 3.

A similar solution is provided for the charge retention problem. More particularly, the solution to the charge retention problem is identical to the solution to the parasitic capacitance problem except that the timing and magnitude of transitions for offsetting the charge retention are different from the timing and magnitude of transitions for compensating for parasitic capacitance. The magnitude will depend on the amount of charge retained. In the illustrated embodiment, offset is applied from a time during acquisition, before settling, until a time during reset. Charge retention is offset by instructing the detector controller 48 to turn a row (other than the row being read) off by a magnitude sufficient to accommodate for charge retention; e.g., a row other than the row being read is provided with a transition from $-V_{off}$ to a negative voltage which is more negative than $-V_{off}$. In order to minimize the range of voltages required to be provided by the detector controller 50 to the array, a number of rows are preferably used to provide the offset, and the magnitude of the negative transition provided on the number of rows is scaled down by the ratio of rows providing compensation to the magnitude of the offset required to accommodate for charge retention. For example, in the preferred embodiment illustrated in FIG. 6, a transition is made from $-V_{off}$ to a negative voltage $-V_{offh2}$ simultaneously on a plurality K of rows other than the row being read. See FIG. 6.

Certain of the rows can be used to provide compensation for parasitic capacitance, and other rows can be used to provide offset for charge retention. The rows not being read can be divided up in any manner to provide compensation and offset. It is also possible that one row could be used to provide both compensation and offset. (Or, if it is desired to minimize the range of voltages required by the array, a set of rows could be used, with the magnitude of transitions reduced at each row of the set, and this set of rows could be used to provide both compensation and offset.)

Figure 7:
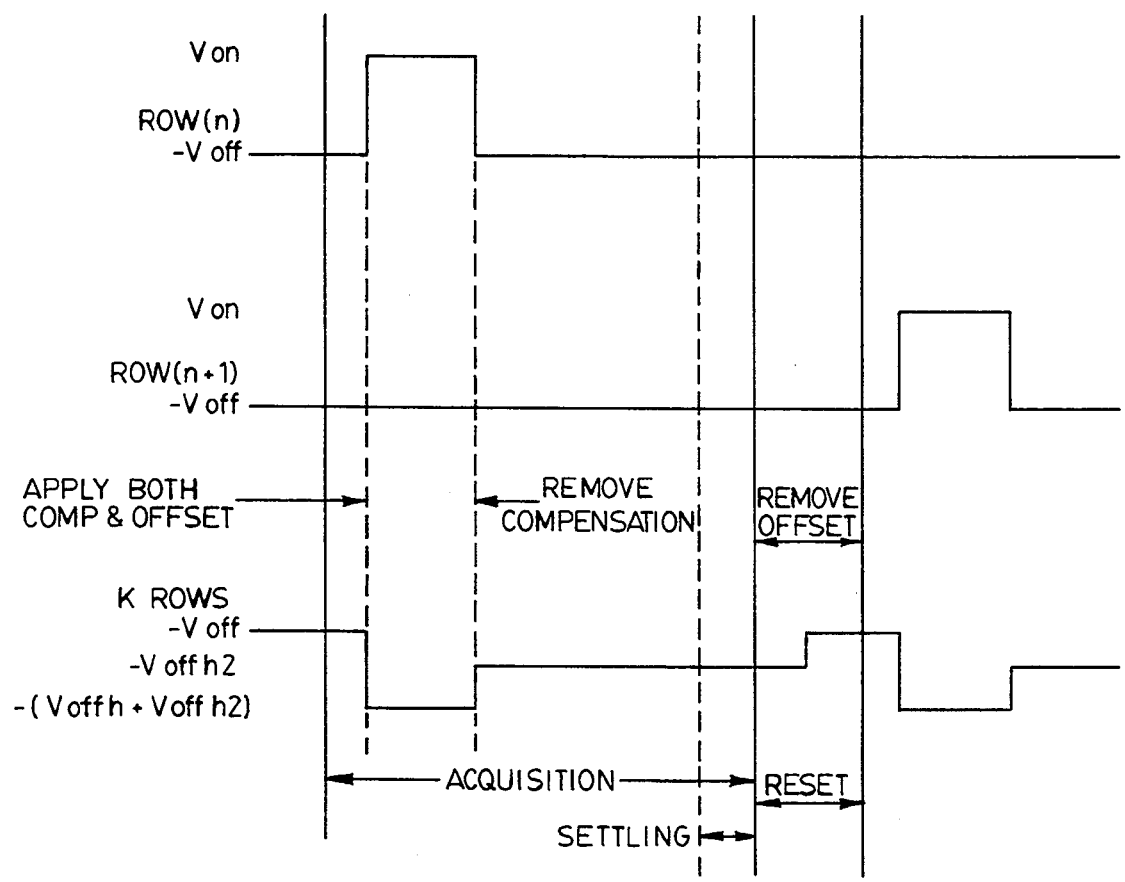
FIG. 7 is a timing diagram illustrating the application of both compensation and offset, in accordance with the invention, in the use of the array of FIG. 3.

FIG. 7 illustrates the simultaneous application of both compensation and offset.

The above described voltages applied to the row electrodes and column electrodes, in the above described timing arrangement, are generated by the detector controller 50. The controller 50 could contain a driver such as an Oki MSM-6568 if column voltages are held at negative voltages.

While a preferred embodiment of the invention has been described, by way of example, various modifications will become apparent to one of ordinary skill in the art. For example, resolution can be traded for readout speed by reading more than one row at a time, and combining an equal number of columns to define square pixels. Thus, the scope of the invention is to be limited only by the spirit and scope of the following claims.

We claim:

1. A light imaging system comprising:
   a plurality of row electrodes and column electrodes;
   an array of rows and columns of photo detector elements, each said element including a photo diode having an anode and a cathode, and a transistor having first and second power electrodes and a control electrode for controlling current flow between said first and second power electrodes, said control electrode being connected to one of said row electrodes, said first power electrode being connected to one of said column electrodes, said second power electrode being connected to said cathode of said photo diode, and said anode of said photo diode being connected to a negative voltage $-V_b$;
   means for charging said photo diodes by connecting said column electrodes to a voltage $V_c$ and connecting said row electrodes to a voltage $V_{on}$ which is positive relative to $V_c$;
   means for exposing said array to photons after said charging means charges said photo diodes;
   means for impeding said photo diodes from being recharged, while said exposing means exposes said array to photons and after said exposing means exposes said array to photons, said impeding means including said transistors and including means for connecting said row electrodes, prior to said array being exposed to photons but after said photo diodes are charged, to a voltage which is negative relative to $V_c$ and negative relative to $-V_b$;
   means for sequentially connecting the rows to the voltage $V_{on}$, for a predetermined period of time, after said exposing means exposes said array to photons and after said impeding means impedes said photo diodes from being recharged;
   means for respectively measuring, at the column electrode for each photo diode in the row connected to $V_{on}$ by said connecting means, the charge required to restore the photo diode to its voltage before it was exposed to photons and after it was charged by said charging means, for a period of time longer than the predetermined period of time so as to provide a settling period;
   means for resetting the measuring means during a reset period after the settling period and before the next row is connected to $V_{on}$; and
   means for providing, on a row other than the row being measured by said measuring means, a negative voltage transition, starting when or before the row being measured is connected to $V_{on}$ and ending during the reset period, so as to provide an offset against charge retention by the transistors in the row being measured.

2. A light imaging system in accordance with claim 1 wherein each said transistor is a field effect transistor having a gate defining said control electrode connected to one of said row electrodes, having a drain defining said first power electrode connected to one of said column electrodes, and having a source defining said second power electrode connected to said cathode of said photo diode.

3. A light imaging system in accordance with claim 1 wherein said array includes amorphous silicon.

4. A light imaging system in accordance with claim 1 wherein said measuring means includes means at each column for integrating the measured amount of charge at that column.

5. A light imaging system in accordance with claim 1 wherein said measuring means is unipolar.

6. A light imaging system in accordance with claim 4 wherein each said integrating means comprises an operational amplifier having an inverting input, a non-inverting input, and an output and including a capacitor connected between said output and said inverting input.

7. A light imaging system in accordance with claim 4 and further including analog to digital converter means connected to each said integrating means for converting the output from said integrating means to a digital signal.

8. A light imaging system in accordance with claim 1 wherein said measuring means simultaneously measures the charge required to restore the charge to each photo diode in the row.

9. A light imaging system in accordance with claim 1 wherein said providing means provides simultaneous negative transitions on a plurality of rows other than the row being measured by said measuring means.

10. A light imaging system in accordance with claim 1 and further comprising compensation means for providing a negative transition on a row other than the row being measured by said measuring means, a negative voltage transition of equal magnitude to the transition from $-V_{off}$ to $V_{on}$, while the row being measured is connected to $V_{on}$, so as to provide compensation for signals caused by parasitic capacitance between the row electrodes and column electrodes.

11. A light imaging system in accordance with claim 1 and further comprising compensation means for providing simultaneous negative transitions, on rows other than the row being measured by said measuring means, having respective magnitudes which add up to the magnitude to the transition from $-V_{off}$ to $V_{on}$, while the row being measured is connected to $V_{on}$, so as to provide compensation for signals caused by parasitic capacitance between the row electrodes and column electrodes.

12. An x-ray imaging system comprising:
a plurality of row electrodes and column electrodes;
an array of rows and columns of photo detector elements, said array including amorphous silicon, each said element including a photo diode having an anode and a cathode, and transistor means having first and second power electrodes and a control electrode for controlling current flow between said first and second power electrodes, said control electrode being connected to one of said row electrodes, said first power electrode being connected to one of said column electrodes, and said second power electrode being connected to said cathode of said photo diode, and said anode of said photo diode being connected to a negative voltage;
means for charging said photo diodes;
means for exposing said array to photons after said charging means charges said photo diodes;
means for impeding said photo diodes from being recharged, while said exposing means exposes said array to photons and after said exposing means exposes said array to photons, said impeding means including said transistor means;
means, operable after said exposing means and said impeding means, for respectively measuring the charge required to restore each photo diode to its voltage before it was exposed to photons and after it was charged by said charging means; and
means for providing an offset against charge retention by the transistor means that are connected to the photo diodes being measured while said measuring means measures the charge required to restore at least one of said photo diodes.

13. An x-ray imaging system in accordance with claim 12 wherein each said transistor means includes a field effect transistor having a gate defining said control electrode, having a drain defining said first power electrode, and having a source defining said second power electrode.

14. An x-ray imaging system in accordance with claim 12 wherein the measuring means includes means for integrating the amount of charge measured for each photo diode.

15. An x-ray imaging system in accordance with claim 12 wherein said measuring means is unipolar.

16. An x-ray imaging system in accordance with claim 14 wherein each said integrating means comprises an operational amplifier having an inverting input, a non-inverting input, and an output and including a capacitor connected between said output and said inverting input.

17. An x-ray imaging system in accordance with claim 14 and further including analog to digital converter means connected to each said integrating means for converting the output from said integrating means to a digital signal.

18. An x-ray imaging system in accordance with claim 12 wherein said measuring means simultaneously measures the charge required to restore the charge to each photo diode in one of said rows.

19. An x-ray imaging system in accordance with claim 18 wherein said providing means provides simultaneous negative transitions on a plurality of rows other than said row being measured by said measuring means.

20. A method of reading image data from an array of rows and columns of photo detector elements that have been exposed to photons, each element including a photo diode having an anode and a cathode, and electronic valve means having first and second power electrodes and a control electrode for controlling current flow between the first and second power electrodes, the control electrode being connected to one of the row electrodes, the first power electrode being connected to one of the column electrodes, the second power electrode being connected to the cathode of the photo diode, and the anode of the photo diode being connected to a negative voltage, said method comprising:
respectively measuring the charge required to restore each photo diode in one of the rows to its voltage before it was exposed to photons; and
providing, on a row other than the row being measured, a voltage transition to at least partially offset against charge retention by the transistors in the row being measured.

* * * * *